(12) United States Patent
Cannon

(10) Patent No.: US 12,089,924 B2
(45) Date of Patent: Sep. 17, 2024

(54) CONTAINER FOR DETERMINING BODY COMPOSITION AND METHOD

(71) Applicant: PHYSICS IP, INC., Midland, GA (US)

(72) Inventor: Sterling L Cannon, Midland, GA (US)

( * ) Notice: Subject to any disclaimer, the term of this patent is extended or adjusted under 35 U.S.C. 154(b) by 699 days.

(21) Appl. No.: 17/381,015

(22) Filed: Jul. 20, 2021

(65) Prior Publication Data
US 2021/0345908 A1    Nov. 11, 2021

Related U.S. Application Data

(63) Continuation-in-part of application No. 16/168,645, filed on Oct. 23, 2018, now Pat. No. 11,213,222, which is a continuation-in-part of application No. 16/027,246, filed on Jul. 3, 2018, now Pat. No. 11,064,943.

(60) Provisional application No. 62/570,570, filed on Oct. 10, 2017.

(51) Int. Cl.
*A61B 5/093* (2006.01)
*A61B 5/00* (2006.01)
*G16H 50/30* (2018.01)
*G01N 33/18* (2006.01)

(52) U.S. Cl.
CPC ............ *A61B 5/093* (2013.01); *A61B 5/7225* (2013.01); *A61B 5/742* (2013.01); *G16H 50/30* (2018.01); *A61B 2560/0252* (2013.01); *A61B 2560/0257* (2013.01); *G01N 33/18* (2013.01)

(58) Field of Classification Search
None
See application file for complete search history.

(56) References Cited

U.S. PATENT DOCUMENTS

| | | | | |
|---|---|---|---|---|
| 3,821,950 A | * | 7/1974 | Boehringer | A61B 5/093 600/541 |
| 4,787,627 A | * | 11/1988 | Daubenspeck | A61B 5/087 482/13 |
| 4,873,866 A | * | 10/1989 | Fairbanks | G01N 9/10 73/437 |

(Continued)

OTHER PUBLICATIONS

Patterson, P. E., and Matthew Distel. "Development of an underwater weighing system for determining body composition." Biomedical Sciences Instrumentation 34 (1997): 363-367. (Year: 1997).*

*Primary Examiner* — Puya Agahi
*Assistant Examiner* — Jairo H Portillo
(74) *Attorney, Agent, or Firm* — Steven C. Stewart

(57) ABSTRACT

A method and apparatus to determine body composition of a subject is disclosed. Physical characteristics of a subject and water in a pool is determined. A body of the subject is completely submerged in the pool of water such that a head of the subject is just below a surface of the water in the pool. The subject completely exhales air into an air measuring device as the body of the subject is submerged just below the surface of the water. A semi-rigid strip or tab portion may be coupled to the air measuring device to indicate when air pressure within the air measuring device is between a predetermined range. The body composition is then determined based on the determined subject characteristics, water characteristics and the amount of air exhaled into the air measuring device when the air pressure is between the predetermined range.

11 Claims, 8 Drawing Sheets

(56) References Cited

U.S. PATENT DOCUMENTS

| | | | | |
|---|---|---|---|---|
| 2014/0323836 | A1* | 10/2014 | Kusukame | A61B 5/00 600/300 |
| 2016/0287139 | A1* | 10/2016 | Luttrell | A61M 16/0006 |
| 2018/0000348 | A1* | 1/2018 | Bishara | A61B 5/6806 |

* cited by examiner

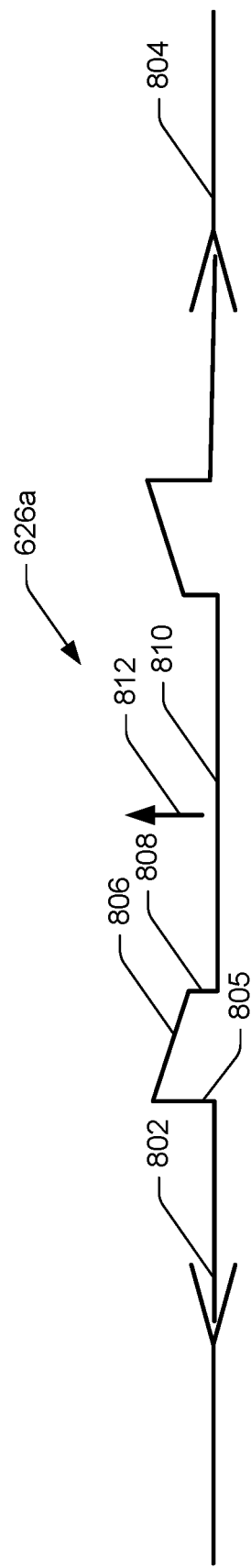
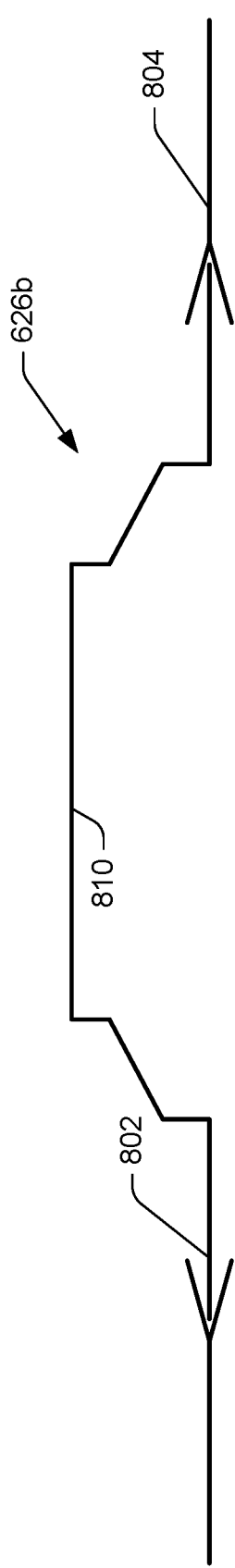
Fig. 8A
Fig. 8B

CONTAINER FOR DETERMINING BODY COMPOSITION AND METHOD

RELATED APPLICATIONS

This application claims the benefit of U.S. provisional application No. 62/570,570 filed on Oct. 10, 2017, and is a continuation in part of U.S. application Ser. No. 16/027,246 titled "Method and System for Determining Body Composition" and filed on Jul. 3, 2018 the contents of which are hereby incorporated by reference.

TECHNICAL FIELD

These claimed embodiments relate to a container for determining body composition and more particularly to container for determining body composition based on a volume of exhalation of a subject in a neutral buoyancy state in water.

BACKGROUND OF THE INVENTION

A container for determining body composition and method is disclosed.

Exemplary processes to determine accurate body composition require an airtight adiabatic chamber with sensitive air flow and pressure measuring equipment (as in a Bod Pod measuring device), a pool of distilled water of known temperature with an overhanging crane scale and personnel to read the scale while measuring underwater weight (as in traditional hydrostatic weighing). A device using ionizing radiation and sensitive equipment to measure and extrapolate the volume of fat (as in a DEXA scan) or sensitive electronic equipment may also be required to measure impedance of the test subject to electric current (as in body impedance testing). These processes to determine accurate body composition can be an expensive, time-consuming and require elaborate specialized equipment.

SUMMARY OF THE INVENTION

In one implementation, a container is disclosed for determining body composition of a subject. The container may be transparent or translucent with an open end and a closed end and has a length extending longer than its width. The container has a plurality of equally spaced radial demarcations extending from the closed end to the open end to provide a distance measurement when an axis extending through the length of the container is vertically aligned with a face of a subject. The distance measurement may be computed using a first of the demarcations disposed adjacent a point below a nostril of the subject and a second of the demarcations disposed adjacent a top of a head of the subject when the container is vertically aligned. A semi-rigid material may be coupled to the container to indicate when air pressure within the container is between a predetermined range or exceeds a predetermined amount. The container may be operative to receive via the open-end water from a pool and air exhaled from a subject when the subject is at least partially submerged in the pool of water. At least one the equally spaced radial demarcations adjacent to a point where the water in the container contacts air in the container when the strip indicates air pressure within the container is between the predetermined range, may indicate a Buoyant lung volume variable used to determine a Buoyant lung volume of the subject.

In another implementation, a method is disclosed for determining a body composition of a subject. The method includes receiving characteristics of the subject, ambient air characteristics and water characteristics of a pool of water. An air measuring device is provided that includes a translucent and/or transparent material bag having its length longer than its width with an opening at one end and a closure at its other end. The bag may have equally spaced parallel radially aligned markings visible on a surface of the bag with the markings originating from the closed end of the bag and extending on the bag at equally spaced intervals to the open end of the bag. The bag is placed adjacent a head of the subject and using markings on the bag a distance from a top of the head of the subject to a point just below nostrils of the subject is recorded. The subject is floated in the pool of water and exhales sufficient air to cause a body of the subject, including a head of the subject, to completely submerge in a suspended position in the pool of water just below the surface. The subject completely exhales air into the air measuring device as the body of the subject is submerged below the surface of the water. Water is transferred from the pool into the air measuring device as air is exhaled by the subject into the air measuring device. The air measuring device containing the transferred water and the exhaled air is squeezed until an indicator that is integrally coupled to the bag indicates that air pressure within the bag is between a predetermined pressure range. A marking on the container adjacent where the surface of the water in the air measuring device contacts the exhaled air is read when the indicator indicates that air pressure within the bag is between the predetermined pressure range. A body composition or an underwater weight of the subject is computed based on the determined subject characteristics, the recorded distance, the water and air characteristics and the read marking.

In another embodiment, an air volume measuring device to measure a residual lung volume in a body of a subject is provided. The air volume measuring device includes a translucent expandable container with an open end and a closed end. The container may have a length extending longer than its width. A semi-rigid strip or object may be coupled to the container to indicate when air pressure within the container is between a predetermined range or exceeds a predetermined pressure. The container has equally spaced radial demarcations extending from the closed end to the open end. One of the demarcations indicate a distance from a point below a bottom of a nose to the top of a head of the subject when the container is placed adjacent the subject. Another of the demarcations to indicate a residual lung volume variable when the semi-rigid strip indicates that air pressure within the container is between a predetermined pressure range. The residual lung volume variable corresponds to a measured volume of air exhaled by the subject when the subject exhales air expanded within the body resulting from the subject moving from a deeper depth to a shallow depth in a pool of water after the subject empties air from its lungs into the pool at the deeper depth.

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

FIG. 8A is a cross sectional view of the tab shown in FIG. 6 indicating pressure in the container has not reached a predetermined level; and FIG. 8B is a cross sectional view of the tab shown in FIG. 6 indicating pressure in the container has reached a predetermined level.

DETAILED DESCRIPTION

Figure 1A:
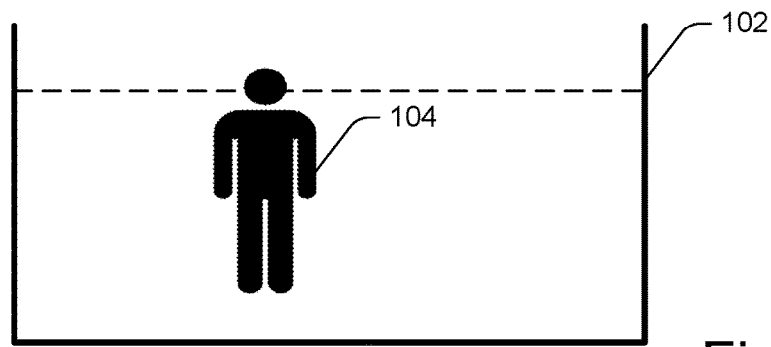
FIGS. 1A-1B are diagrams of a subject in water and exhaling into a container in accordance with the invention.

Referring to FIG. 1A, there is shown a pool 102 of water in which a subject 104 is floating. The subject 104, inhales a normal breath and would float in a normal position where a portion of the head of the subject 104 is above the water.

Figure 1B:
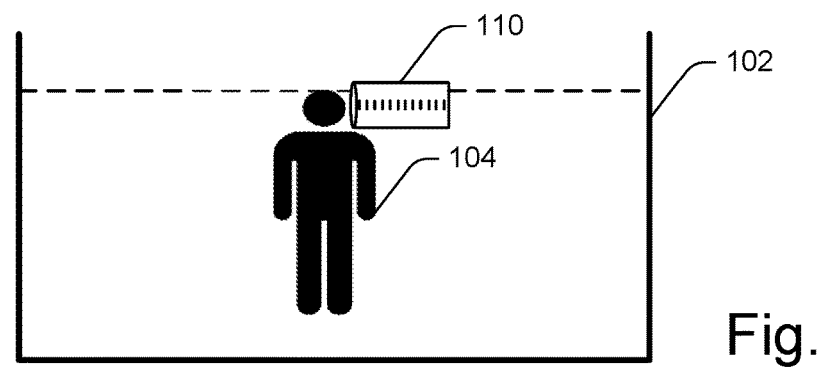

Referring to FIG. 1B, the subject then exhales a small amount of breath into the water such that the top of the subject's head is just below the surface of the water in pool 102. At that point, the subject 104 would completely exhale into an open end of container 110 and manually seal the bottom/open end of the container 110 using the subject's 104 hands so that the container held the exhaled breath of air and water from the pool 102. In one implementation the container 110 is constructed from flexible transparent plastic, is open at one end and sealed at its other end. An exemplary container is shown and described in more detail in connection with FIG. 5. The container may have line markings and numerical at regular equally spaced intervals from the open end of the container to the closed end of the container so that a container volume of air may be determined.

Figure 1C:
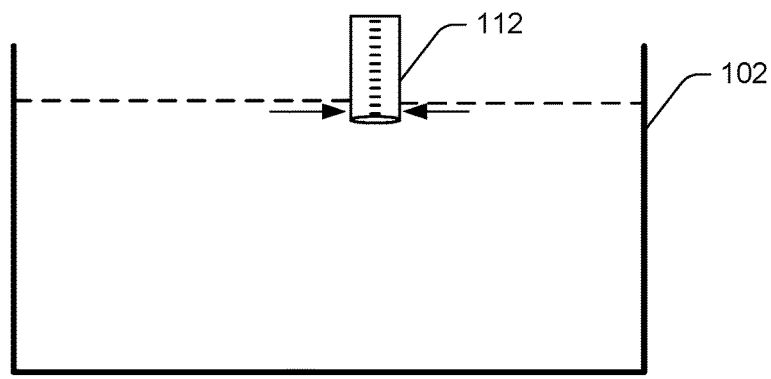
FIG. 1C is a diagram illustrating identifying the volume of the container in FIG. 1B.

Referring to FIG. 1C, the container 110 would then be partially raised above the surface of the water in pool 102. The bottom of the container 110 could then be squeezed so that only a small amount of water would remain in the container, and the air exhaled by the subject would completely fill and expand the portion of the container not including the water. The number of the marking viewable in the air-filled expanded portion of the container just above the surface of water in the container could then be determined. The markings would be provided along with other characteristics of the subject, a water temperature for measurement in distilled or pure water or a direct water density measurement from a hydrometer or similar apparatus, and the volume adjusted for the depth of the orifice through which the air was exhaled to get to neutral buoyancy to a computing device (See FIG. 2) to compute the composition of the body of subject 104 using the method described in FIG. 4.

Figure 2:
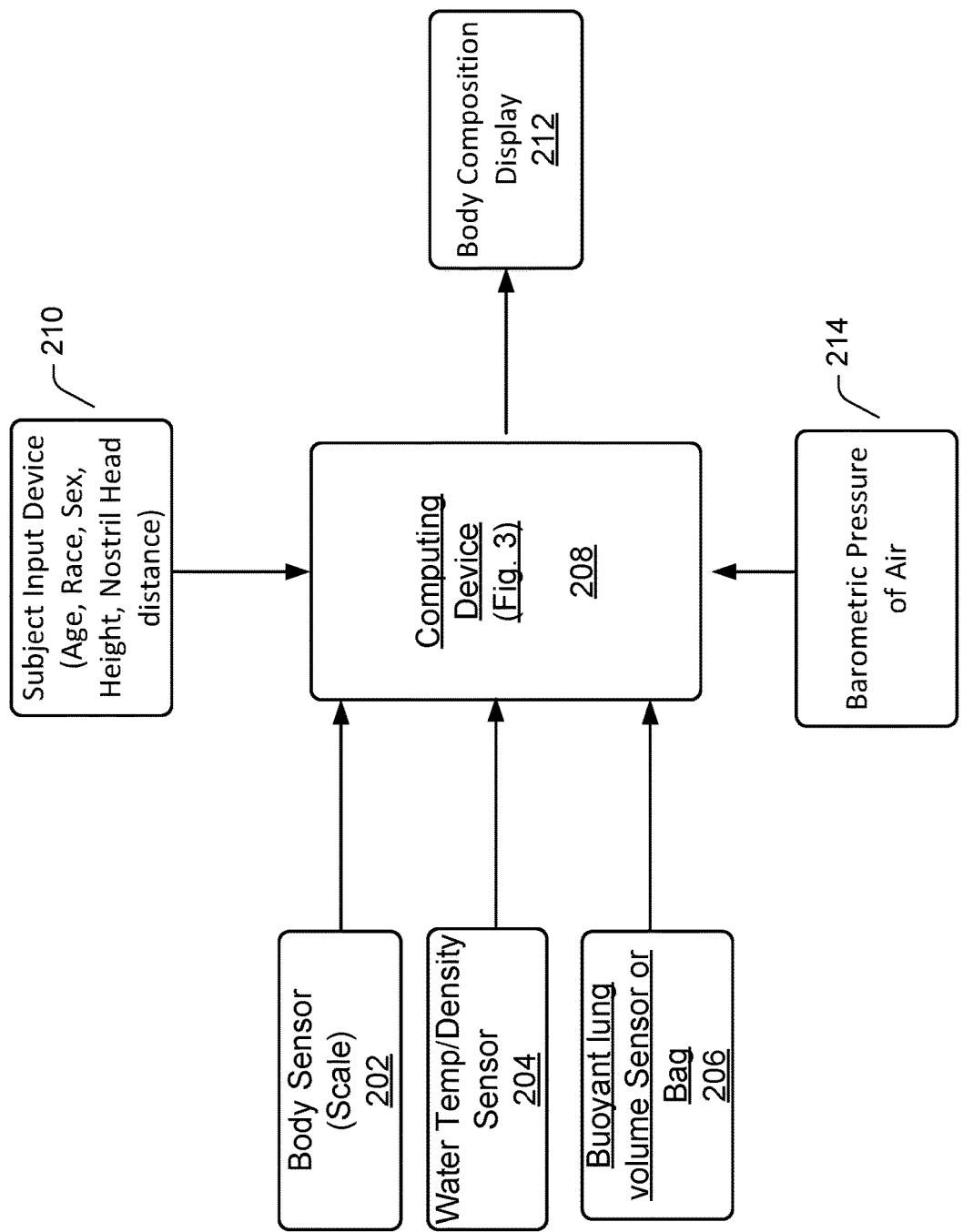
FIG. 2 is a simplified schematic diagram of a system for calculating body composition.

Referring to FIG. 2, there is shown a system 200 for calculating body composition. System 200 includes Body Sensor 202, water temperature sensor or water density measuring device 204, a barometric pressure measuring device 214 (that can be used to measure ambient air pressure), and Buoyant lung volume Sensor or Bag/Container 206 all coupled to Computing Device 208. Computing device 208 is also coupled to subject input device 210 (such as a keyboard, voice detector or other input device) and provides an output of body composition (along with any other computed measurement) to a display device 212.

Body sensor 202 may include a scale or other device that weighs the subject 104 in the air and on land. Water temperature/density 204 sensor may include a thermometer that measure the temperature of the water or a hydrometer that measure the density of water in the pool 102. Sensor 206 may be a regulator connected to a sensor that detects an amount of air and may include a device to measure total dissolved solids in the water. This affects the water density for a given temperature exhaled by the subject. Water density may be measured directly as well with a hydrometer or similar device. An exemplary sensor 206 may include container 110.

In one implementation sensors 202, 204 and/or 206 sends signals to computing device 208 via an electronics network, via a Bluetooth transmitter, or via a telecommunication line. In another implementation sensors 202-206 provide a reading/display 212 that can be read by a user and entered manually via a keyboard or an input/output device 210.

Input device 210 may include a keyboard or other input output device for manual entry of data into computing device 208. Such data may include characteristics of the subject 104 obtained from the subject. Such subject characteristics include Weight, Age, Race (Race may affect fat free body density based on published normative data), Sex, barometric pressure, a height, and distance from a bottom of the subjects Nostril to top of the subject's head. Such distance may be determined by placing one end of container 110 (such as the closed end of the container) to align with the top of the head while placing the other end of the container 110 over the face. A number adjacent a mark on the container 110 at the point below the nostril could indicate a distance from the top of the top of the head to the point below the nostril. This distance could be then input as a below the nostril to top of the head distance into computing device 208 using device 210.

The computing device 208 could transmit an indication of body composition (request for inputs or any other measurement/calculation determined by computing device 208) to display/output device 212.

Figure 3:
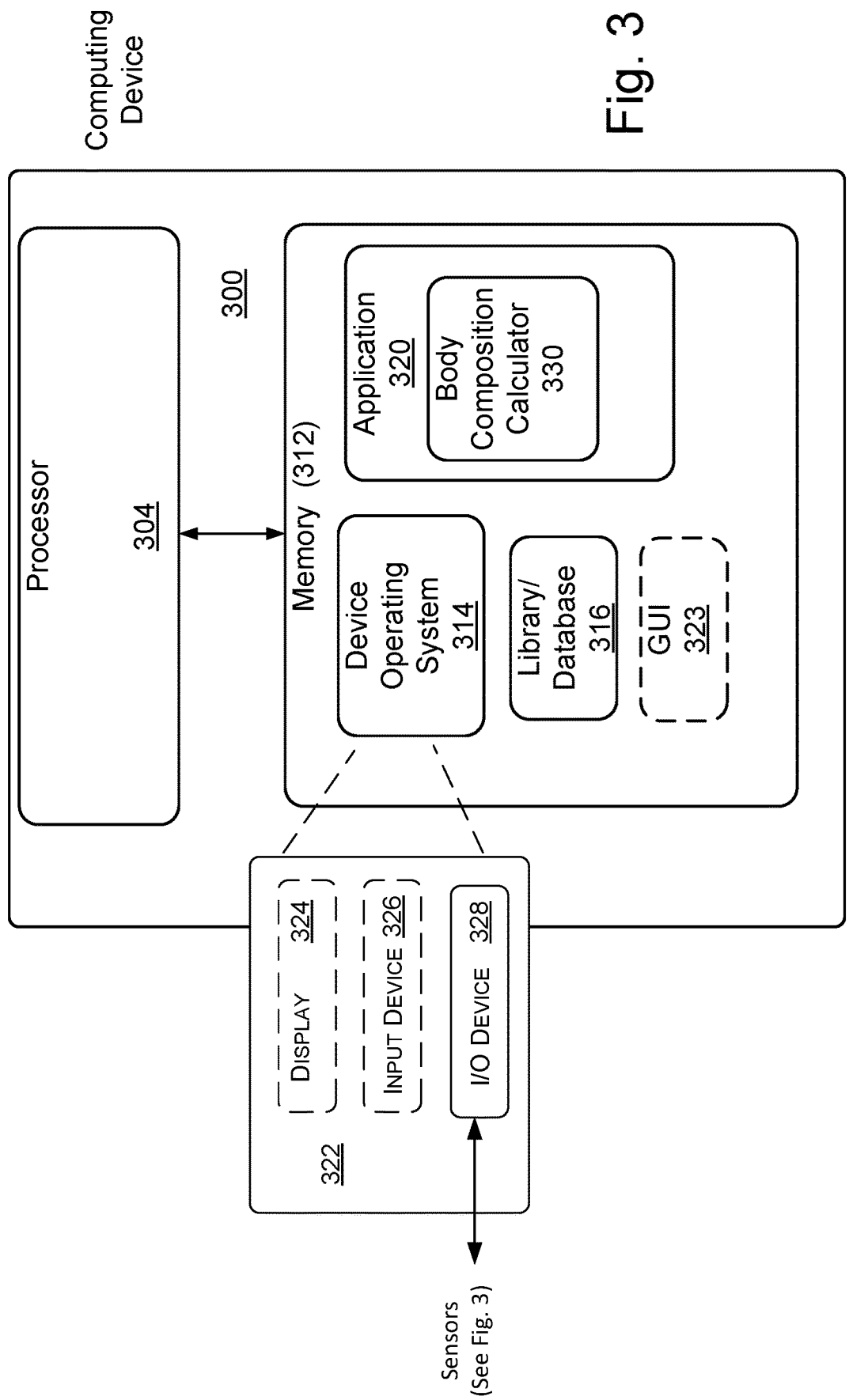
FIG. 3 is a simplified schematic diagram of the computing device shown in FIG. 2.

Referring to FIG. 3, there are illustrated selected modules in computing device 300 (computing devices of FIG. 2). Computing device 300 includes a processing device 304, memory 312, and display/input device 322. Processing device 304 may include a microprocessor, microcontroller or any such device for accessing memory 312 and display/input device 322. Processing device 304 has processing capabilities and memory suitable to store and execute computer-executable instructions. In one example, processing device 304 includes one or more processors.

Processing device 304 executes instructions stored in memory 312, and in response thereto, processes signals from and display/input device 322. Device 322 may include input device 326, network I/O device 328 that includes network and communication circuitry for communicating with a communications network (FIG. 2) and output device 329 for communicating with a printer. Input device 326 (device 210 in FIG. 2) receives inputs from a user of the personal computing device and may include a keyboard, mouse, track pad, microphone, audio input device, video input device, or touch screen display. Display device 324 (device 212 in FIG. 2) may include an LED, LCD, CRT, or any type of display screen.

Memory 312 may include a non-transitory volatile and nonvolatile memory, removable and non-removable media implemented in any method or technology for storage of information, such as computer-readable instructions, data structures, program modules or other data. Such memory includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium (including a non-transitory computer readable storage medium) which can be used to store the desired information, and which can be accessed by a computer system.

Modules stored in memory 312 of the computing device 208 may include an operating system 314, an I/O controller 312, a library 316, an application 320 and a graphical user interface 323. Operating system 314 may be used by application 320 to operate Display 324. Library 316 may include preconfigured parameters (or set by the user before or after initial operation) such as computing device operating parameters and configurations. Application 320 may include a body composition calculator 330 and other code for executing the processes shown or describe in connection with FIGS. 1-2, and FIG. 4.

Figure 4:
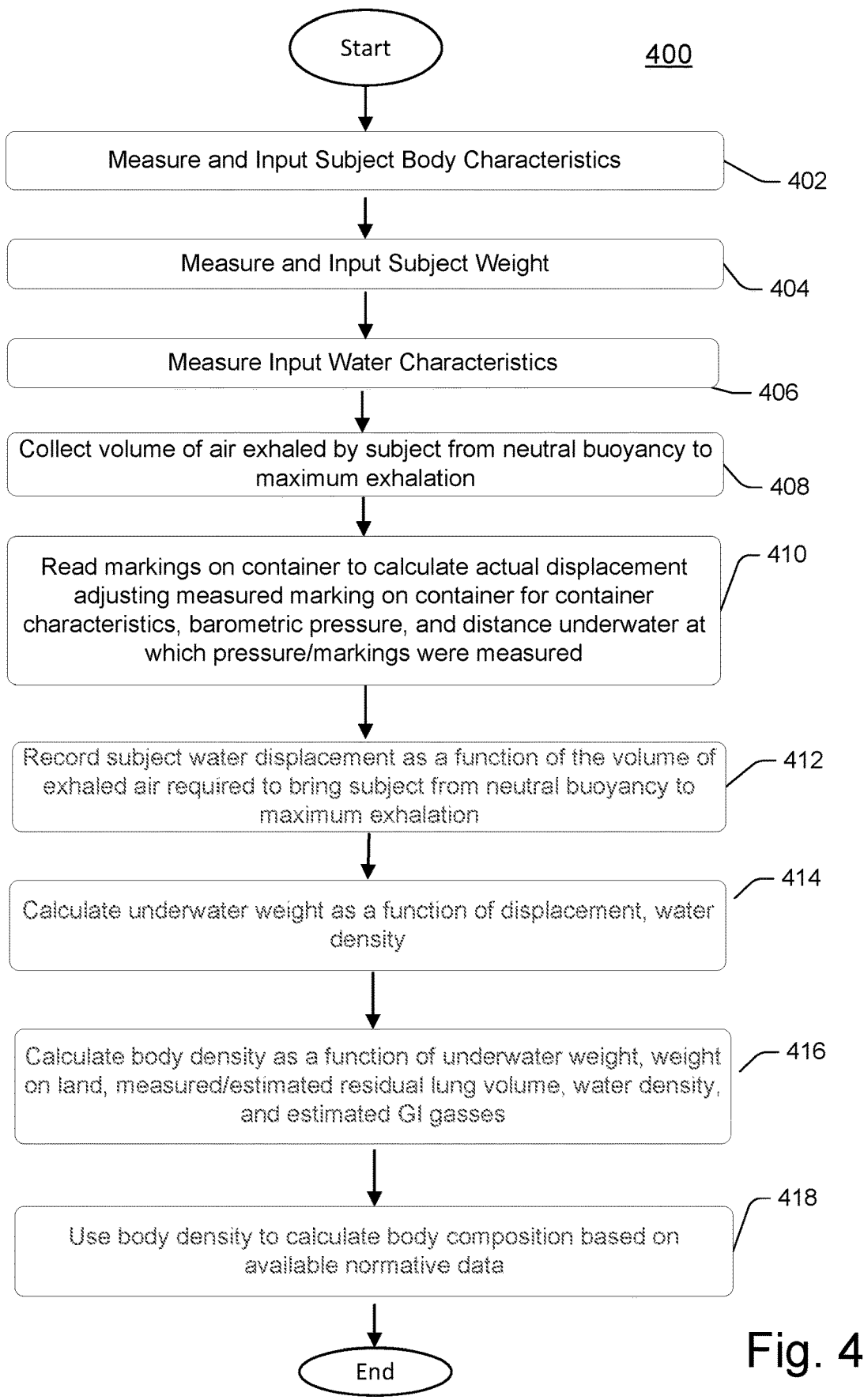
FIG. 4 is a flow chart of the process for determining body composition with the system shown in FIG. 2.

Illustrated in FIG. 4, there is shown a process 400 for determining body composition. The exemplary process in FIG. 4 is illustrated as a collection of blocks in a logical flow diagram, which represents a sequence of operations that can be implemented in hardware, software, and a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the processes are described with reference to FIG. 4, although it may be implemented in other system architectures.

Referring to FIG. 4, a process 400 is shown for determining body composition of a subject using the processor and modules shown in FIG. 3.

In the process, the subjects body characteristics are measured in entered via Input/output device 210 to computing device 208 (FIG. 2) in block 402. The subjects body characteristics may include the subjects: land Weight, Age, Race, Sex, barometric pressure, a height, and distance from a bottom of the subjects Nostril to top of the subject's head In block 404, the subjects land weight is determined using body sensor 202. The body sensor 202 in one implementation is a scale. The body weight is then transferred to computing device 208 (FIG. 2).

In block 406, one of the characteristics of the water is determined. In one implementation, temperature of the water in the pool 102 is determined by water temperature sensor 204 and an estimate of dissolved solid in the water is determined. The temperature is then transferred to computing device 208 (FIG. 2). The density of the water can be measured directly rather than being computed from temperature and estimate of dissolved solids measured from an EC meter.

In block 408, the subject enters a pool of water 102 and exhales enough breath so that the subject's body is completely submerged and suspended in the pool of water, while the subject's entire head is positioned just below the surface of the water. In one implementation, the top of the head of the subject is between 0.1" and 3" below the surface water and the body of the subject is still neutral buoyance state (not moving up or down). While the subject's body and head are submerged and still neutral buoyance state just below the water surface, the subject exhales the rest of the subject's breath into container 110. The volume of air exhaled by the subject from neutral buoyance to maximum exhalation is collected in the container.

Alternately, an electronic breath measuring/recording device senses is used in place of container, which transmits to the computing device the amount of the volume of air exhaled by the subject. Examples of electronic measuring devices include EasyOne® Air spirometer made by NDD Medical Technologies, Inc. company of Andover, MA If an electronic measuring device is used to record the breath exhaled, steps 410-412 are skipped.

If In block 410, the container 110 is placed in an upright position, closed at its open end, and squeezed so that the air fills up the container. The marking on the container 110 at the level of the surface of water in the bag is read and inputted into computing device using input output device 216. This measurement is used to calculate actual displacement adjusting for measured container characteristics, barometric pressure, and distance underwater at which the pressure and markings are measured.

In block 412, the marking on the container, which is a function of the volume of the exhaled air required to bring the subject from neutral buoyance to maximum exhalation, is then converted by computing device 208 into subject water displacement SWD. For this application, Subject Water Displacement, Buoyant lung volume and Subjects' Displacement of water are synonymous. The formula of Displacement Water (DWD) for a container shown in FIG. 5, having a width W, and length L, and diameter D at its open end is as follows:

$DWD = ax^3 + bx^2 + cx + d$ (Polynomial equation) where variables a, b, c, and d are affected by the shape of the bag and the characteristic of the plastic, and x is a Buoyant lung volume variable and demarcation on the bag corresponding to a distance from the closed end of the bag to line on the bag where air meets the water surface, and the air fully expands the bag. The volume measurement on the bag is a measured bag volume but does not equal the buoyant lung volume. The Buoyant lung volume is obtained as a function of the Bag volume measurement, the distance from the top of the head to the nostrils, the inflation pressure of the bag (10 cm $H_2O$ in this case) and the barometric pressure. In one implementation a, b, c, and d may be derived by filling a bag/container to the various demarcations (See FIG. 5) on the bag and recording the volume required to fill too. These volumes may be plotted against the number marking (e.g., 1 cm=20 cc, 2 cm=50 cc, 3 cm=90 cc etc.) on the bag and then used (as variable x) to make a 3rd order polynomial equation to fit a curve. In one implementation, this measurement of DWD is determined using a 6th order polynomial for the first 15 markings (at 1 cm spacings for a 6"×12" bag) and then a linear equation is used for the remainder of the bag volume.

In another implementation the container may be 6" wide, and 12" tall. In such implementation, DWD may be calculated using the Polynomial equation when the exhaled air from the subject fills ⅓ or less of the bag, and may be computed using the formula DWD=Ax+B when exhaled air from the subject fills greater than ⅓ of the container, where A and B are determined by plotting volumes of the container against the number marking (e.g. 1 cm=20 cc, 2 cm=50 cc, 3 cm=90 cc etc.) on the container and then used (as variable x) to make a linear equation to fit a line.

In block 414, the underwater weight (UW) of the subject is calculated as a function of the subject water displacement (DWD) and water density (WD) using the following formulas:

If no assistive device/object is used to add weight to maintain the subject underwater at neutral buoyance, then underwater mass in Kg of the subject, is UW=Buoyant lung volume (DWD)*density of water (WD). In one implementation the density of water may be determined using a formula such as WD=(999.84847+0.06337563*T−0.008523829*T2+0.00006943248*T3−0.0000003821216*T4)/1000 per ITS research, where T-T4 are temperatures. (See ITS-90 Density of Water Formulation for Volumetric Standards Calibration, published in Volume 97, Number 3, in May 1992 in the Journal of Research of the National Institute of standards and technology, authored by Jones and Harris, the contents of which are hereby incorporated by reference.

The density of water WD=Density for a given concentration of salt in weight % (C)=(750.2834+26.7822*C+−0.26389*$C^2$)+(1.90165+−0.11734*C+0.00175*$C^2$)*T+(−0.003604+0.0001701*C+−0.00000261*$C^2$)*$T^2$). The calculation for density of water with NaCl is good for saltwater swimming pools and could incorporate another input device to measure the Total Dissolved Solids (TDS). One such device to measure the Total Dissolved solids is a TDS Water Tester marketed under the brand name of PATEA™ by Ye Shun Cai of Huanggang Town, Raoping Count No. 5 Shanxiading Fengwei Guangdong CHINA.

If an assistive device/object is used to maintain the subject at neutral buoyance, then underwater mass in Kg of the subject, is UW=(Buoyant lung volume DWD*density of water WD)−((Mass of the object in air−(Volume of the object*density of water WD)). The Buoyant lung volume (DWD) is the volume of air expired to take the subject from neutral buoyancy to full expiration.

In block 416, the body density (BD) of the subject is calculated as a function of the underwater weight (UW), weight of the subject on land (SW), measured and/or estimated residual lung volume (RLV), pool water density (PWD) at the pool water temperature (WTemp), and estimated Gastral Intestine Gas (GI Gas). Such body density (BD) is calculated by computer 208 using the following formula:

BD=(Mass of subject in air (SW))/(((Mass of subject in air (SW)−Mass of subject submerged (UW))/Density of water (WD))−(Residual volume in L (RLV)+0.1 L to account for GI gas)); i.e., BD=SW/(((SW−UW)/WD)−(RLV+0.1 L)).

In block 418, the determined body density (BD) is used to calculate body composition (BC) based on available normative data. In one implementation the body composition is calculated using the following formula:

BC=((a/Body density(BD))−b)*100 where a and b are constants determined by normative data published for age and race matched subjects or obtained by measurement with another device such as a DEXA scan whose readings can then be compared to the body density as measured using this method. The resulting "density of fat free body mass" can then be used to obtain a personalized a and b constants for use in future measurements. See Siri, W. E. (1961). Body composition from fluid space and density. In J. Brozek & A. Hanschel (Eds.), Techniques for measuring body composition (pp. 223-244). Washington, DC: National Academy of Science; and Brozek, J., Grande, F., Anderson, J. T., & Keys, A. (1963). Densitometric analysis of body composition: Revision of some quantitative assumptions. Annals of the New York Academy of Sciences, 110, 113-140, the contents of which are hereby incorporated by reference.

The computing device 208 may then send the determined body composition to indicator 212 for display.

Figure 5:
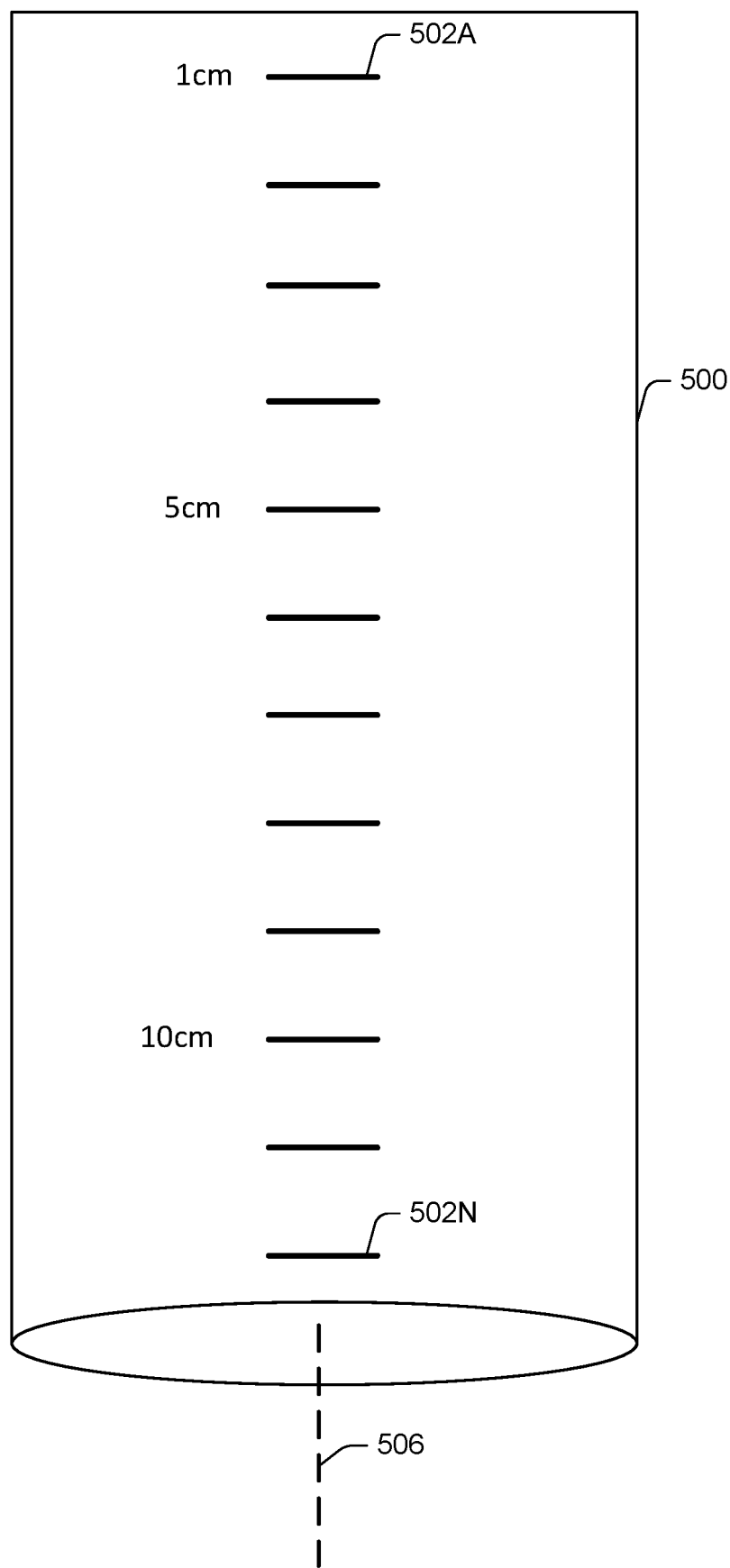
FIG. 5 is an isometric diagram of an exemplary container shown in FIGS. 1B-1C and used to determine body composition.

Referring to FIG. 5, there is shown an exemplary container 500 (Container 110 in FIGS. 1b-1c), for holding exhaled air of the subject. The container 500 may be a bag made from a flexible transparent plastic material preferably having a length greater than its width. Container 500 may be closed/sealed at one end and open (unsealed) at the other end. An axis 506 may extend through a center and along a length of the container 500 from the closed end to the open end. When the container 500 is oriented in a vertical position, visible radially extending horizontal Markings 502A-502N (also referred to as demarcations) may be placed at equal intervals in a row from the sealed end to the open end around the axis 506. Sequential numerical numbers may be placed adjacent each of the markings 502A-502N indicating a distance on container 500 from the adjacent demarcations to the sealed/closed end of the container 500.

If the sealed end of the container 500 was placed at a level of the top of the head of the subject and the container 500 was placed adjacent to the front of the face of the subject, one of the numerical numbers (502A-502N) adjacent a marking just below the nose/nostrils of the subject could be read to determine the distance from the top of the head of the subject to the point on the subject just below the nose of the subject. In addition, if the subject exhales into an empty container 500 while submerged in water (as described previously), and the container 500 is subsequently closed at the open end (and squeezed tight to prevent leakage from the open end), the exhaled air and water in the container 500 will substantially fill the container 500.

The one of the numbers (502A-502N) adjacent the marking at the position just above the surface of the water in the container 500 can be viewed and used as previously described to calculate the subject water displacement (SWD). In one implementation this number will correspond to a distance in inches and/or centimeters from the closed end of the container to the surface of the water in the container 500. In another implementation, the container's 500 internal air inflation pressure may be measured or estimated using a pressure sensor.

Figure 6:
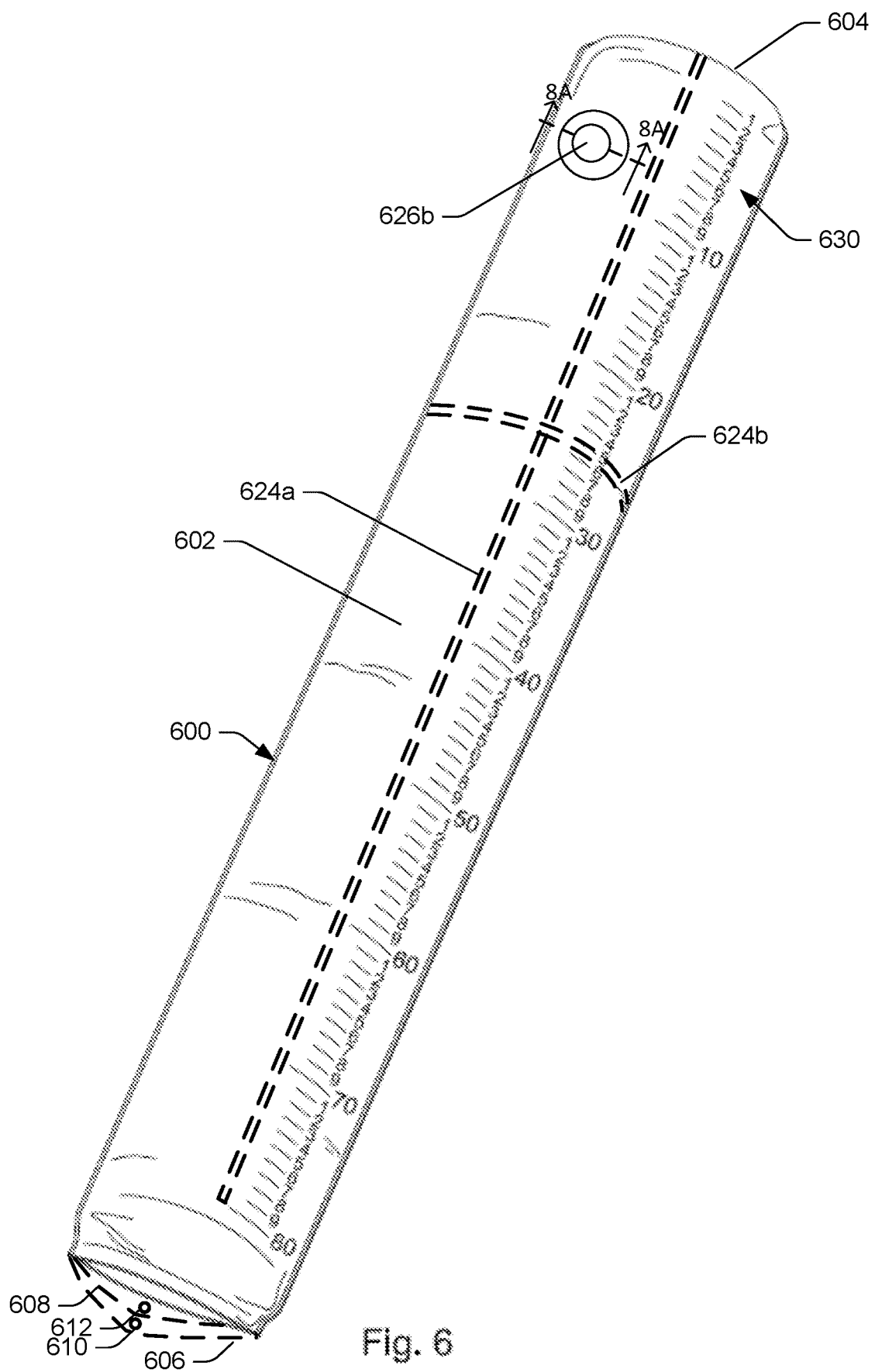
FIG. 6 is an isometric view of an alternate embodiment of the container shown in FIG. 5 after containing air and/or water.
Figure 7:
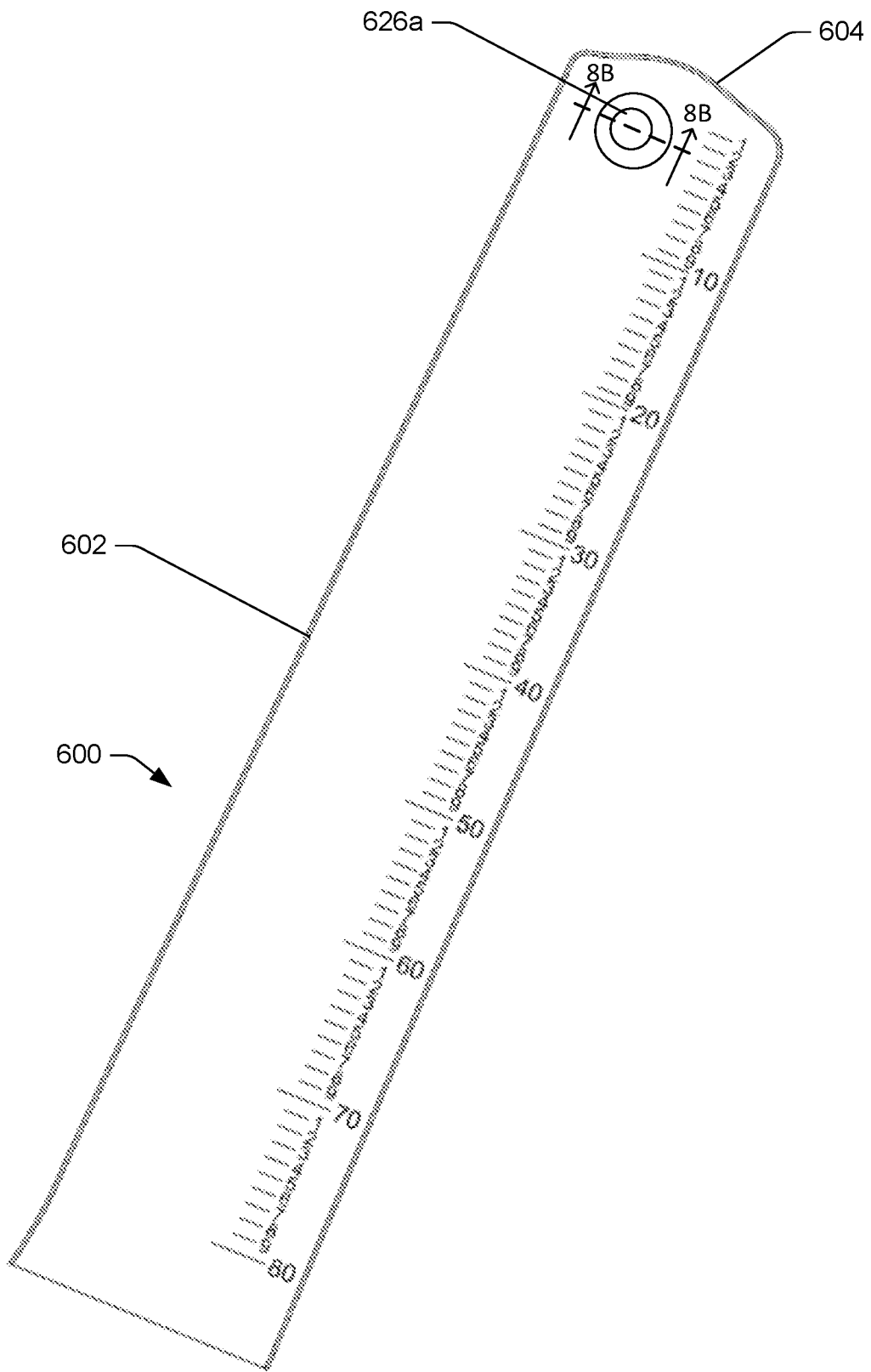
FIG. 7 is an isometric view of the exemplary container shown in FIG. 6 without air or water.

Referring to FIGS. 6 and 7, there is shown container 600, which is an alternate embodiment of container 500. In one implementation container 600 is constructed from a thermoplastic polyurethane material (preferably manufactured by BASF SE of Ludwigshafen, Germany) and has a textured outside surface 602 to improve griping. Embedded in plastic of the container 600 is an antimicrobial material.

Referring to FIG. 6, one end of the container 600 is closed and has a contoured edge 604. Another end of container 600 is open optionally having tabs 606 and 608 respectively having holes 610 and 612 for handing container 600.

Volumetric expansion of container 600 is calibrated at a certain temperature with predictable changes in volume with changes in temperature (volumetric calibration consistent for given temperatures). This permits the container 600 to be attachable to a breathing tube or to be able to be used without one. In one implementation container 600 has a predictable fill pressure endpoint that is detectable by alteration in one or more folds on the container 600. Alternately container 600 may be calibrated as described herein.

Container 600 may optionally include a pressure sensor 624a embedded in a wall 608 and extending laterally from one end of container 600 to adjacent the open end of container. Container 600 may optionally include a pressure sensor 624b embedded in a wall 602 and extending radially. Pressure sensors 624a and 624b may crinkle when the pressure in container 600 is below a predetermined range and may warp or separate from wall 602 of container 600 when the pressure in container 600 is above the predetermined pressure range.

Sensor (e.g., sensor 624a or 624b) could also be a mechanical device or an electronic one. In one implementation the sensor is mechanical, liquid crystal chemical, or electronic to aid in volumetric calibration or a determination that the container is at the correct temperature to read the pressure in the container 600. The pressure sensor may be a separate internal device contained within the container 600 that will indicate with light, sound, or color when an appropriate inflation pressure is reached when squeezing the inflated container 600.

Referring to FIGS. 6 and 8A, a tab pressure indicator 626 may be embedded on one end adjacent edge 604 of container 600 and may be used to indicate that pressure in the container is within a predetermined range or exceeds a predetermined pressure threshold. Indicator 626 is preferably circular shaped having an outside edge 802 that couples with container 804 (600 FIGS. 6 and 7) to from a tight seal. Indicator 626 has a first wall 805 coupled via ledge portion 806 and via second wall 808 to plateau portion 810. Referring to FIGS. 8A and 8B, when pressure in container 802 exceeds a predetermined threshold, flat plateau portion 810 expands in the direction of arrow 812, along with ledge portion 806 and second wall 808 to form and expanded position (See FIG. 8B) indicating the pressure in container 802 has met a predetermined minimum level and/or is between a specific pressure range. When the pressure in container 802 exceeds the predetermined range, the plateau portion 810 will bow outward and will cease to remain flat.

Referring to FIG. 6, the demarcations 630 on the container 600 may be a consistent 1 cm apart with inherent errors and tolerances that will introduce errors in the volumetric measurements on the bag. The seal on the edges of the container 600 may vary in distance from each other or the printing may be stretched or contracted from, increasing, or decreasing the volume between demarcations a calculatable percent. Container 600 may then be calibrated using with a hanging scale, hydrometer/refractometer/pycnometer, thermometer, and water as follows.

The reference container 600 volumetric polynomial equation and temperature adjustment may be stored in a computing device and the expected volumes at various markings are known. The container may then be weighed dry using the holes 610 and 612 disposed adjacent the base (open end) of the container 600.

Water in a pool (See FIG. 1) may be measured for density and temperature. The container 600 may then be submerged in the water to acclimate container 600 to the water temperature.

The container 600 may be filled with water from the pool in an inverted orientation (closed end 604 down) to a first known demarcation>5 cm from the apex (at which time the volume between demarcations becomes a linear equation) while inflated to the appropriate inflation pressure as defined by the previously described container pressure measuring procedure.

The container 600 may then be allowed to deflate. A hanging scale may be used to measure the weight of the water and container 600 when hanging from the small holes 610 and 612 located in the base (open) portion of the container 600.

The volume of the water in container 600 may be calculated using the formula: Water in Container=((weight of water+bag)−(weight of bag))/density of the water.

The container 600 may then be filled with more water until the water can be read on a larger known demarcation while air in the container 600 is inflated (by squeezing container at one end) to the appropriate inflation pressure.

The volume of the water in container 600 is re-calculated using the formula:

$$\text{Water in container} = ((\text{weight of water+bag}) - (\text{weight of bag}))/\text{density of the water}.$$

The calibration (expected error adjustment) may then be computed as follows:

The expected volume based on the reference container is calculated for the 1st and 2nd demarcations using the formula: Demarcation adjusted for temperature=Observed Demarcation Number*$(1+((-0.000037289799497185*\text{temp in Celcius}^2)+(0.00286541085100888*\text{temp in Celsius})-0.0527112272420577))$, and Expected volume= $(76.885*\text{Demarcation adjusted for temperature})-74.426)$ A multiplier is determined using the formula: Multiplier= ((Observed volume 2−observed volume 1)−(Expected volume 2−Expected volume 1))/(Expected volume 2−Expected volume 1).

The multiplier is then used as a multiplier adjustment to the demarcations in subsequent body fat measurements per the previously describe body fat determination method.

The sample bag volume adjusted for seal and stretch errors using the formula: Expected volume based on measurement demarcation and reference bag equations*(1+multiplier adjustment).

While the above detailed description has shown, described and identified several novel features of the invention as applied to a preferred embodiment, it will be understood that various omissions, substitutions and changes in the form and details of the described embodiments may be made by those skilled in the art without departing from the spirit of the invention. Accordingly, the scope of the invention should not be limited to the foregoing discussion but should be defined by the appended claims.

What is claimed is:

1. A method for determining a body composition of a subject comprising:
  receiving characteristics of the subject, ambient air characteristics and water characteristics of a pool of water, the pool of water having a surface;
  providing an air measuring device that includes a translucent material bag having its length longer than its width, the translucent material bag having an opening at one end and a closure at its other end, the translucent material bag having a plurality of equally spaced parallel radially aligned markings visible on a surface of the bag, the markings originating from the closed end of the bag and extending on the translucent material bag at equally spaced intervals to the open end of the translucent material bag;

placing the translucent material bag adjacent a head of the subject and recording using markings on the translucent material bag a distance from a top of the head of the subject to a point just below nostrils of the subject;

floating the subject in the pool of water;

exhaling sufficient air by the subject to cause a body of the subject, including a head of the subject, to completely submerge in a suspended position in the pool of water just below the surface;

completely exhaling air by the subject into the air measuring device as the body of the subject is submerged below the surface of the water;

transferring water from the pool into the air measuring device as air is exhaled by the subject into the air measuring device;

squeezing the air measuring device containing the transferred water and the exhaled air until an indicator that is integrally coupled to the bag indicates that air pressure within the translucent material bag is within a predetermined pressure range;

reading a marking on the container adjacent where the surface of the water in the air measuring device contacts the exhaled air when the indicator indicates that air pressure within the translucent material bag is within the predetermined pressure range;

determining a body composition or an underwater weight of the subject based on the determined subject characteristics, the recorded distance, the water and air characteristics and the read marking.

2. The method as recited in claim 1 wherein the characteristics of the subject include the subject's weight, the subject's age, the subject's race, the subject's sex, and the subject's height.

3. The method as recited in claim 1, wherein the water and air characteristics include an air temperature, a barometric pressure and at least one of either (a) a water temperature and an amount of total dissolved solids in the water, or (b) a density of the water.

4. The method as recited in claim 1, wherein the amount of air exhaled into the bag (DWD) is determined at least partially using the equation $ax^3+bx^2+cx+d$, wherein a, b, c, and d, are predetermined constants, and wherein x is a distance designated by a marking on the bag where air exhaled by the subject into the open end of the bag to fully expand the bag contacts a surface of water remaining in the bag upon the subject completely exhaling air into the bag when the body of the subject is submerged below the surface of the water.

5. The method as recited in claim 1, wherein the body composition (BC) of the subject is determined using the equation:

BC=(x/(BD)−y)*100, where BD is body density of the subject and x and y are constants determined by normative data published for age and race matched subjects, and where BD=SW/(SW UW/WD−(RLV)+0.1 L to account for GI gas)), where UW=(BLV)*(WD), where SW is the weight of subject on land, UW is the mass of subject submerged, WD is the density of water, RLV is residual volume in liters, and BLV is buoyant lung volume.

6. The method as recited in claim 1, wherein the underwater weight of the subject is determined using the equation UW=Buoyant lung volume (BLV)*density of water (WD), where BLV is a function of the bag measurement, barometric pressure, and distance from the top of head to nostrils of the subject and a bag inflation pressure.

7. An air volume measuring device to measure a residual lung volume in a body of a subject, the air volume measuring device comprising:

a translucent expandable container with an open end and a closed end, the container having a length extending longer than its width;

a semi-rigid strip coupled to the container to indicate when air pressure within the container is between a predetermined range;

the container having a plurality of equally spaced radial demarcations extending from the closed end to the open end, a first of the demarcations to indicate a distance from a point below a bottom of a nose to the top of a head of the subject when the container is placed adjacent the subject, and a second of the demarcations to indicate a residual lung volume variable, when the semi-rigid strip indicates that air pressure within the container is between a predetermined pressure range, corresponding to a measured volume of air exhaled by the subject when the subject exhales air expanded within the body resulting from the subject moving from a deeper depth to a shallow depth in a pool of water after the subject empties air from its lungs into the pool at the deeper depth; and a lung volume electronic computing device to determine residual lung volume based on a reading of the at least one of the radial demarcations indicating the residual lung volume variable in response to the strip indicating the air pressure within the container is between the predetermined range, wherein the lung volume electronic computing device further comprises:

circuitry to receive a) a determined ambient air pressure from an air pressure measurement device, b) a determined water density from a measurement device operative to measure water density of water in the pool, c) a measurement corresponding to the shallow depth of the subject, d) a measurement corresponding to the deeper depth of the subject, and e) the residual lung volume variable of the subject; and circuitry to determine a residual lung volume (V1) of the subject based on the received a) determined ambient air pressure, b) the determined water density, c) the measurement of the shallow depth, d) the measurement of the deeper depth, and e) the measured volume of any potentially remaining air exhaled by the subject (MVOA) at the shallow depth after exhaling air by the subject at the deeper depth.

8. The air volume measuring device of claim 7, further comprising:

a tube having an opening at a first end, and a mouthpiece at its other end, the tube operative to be inserted into the container at the first end to enable a mouth of the subject to contact the mouthpiece to exhale air via the tube into the container to expand walls of the container from a collapsed configuration to an expanded configuration.

9. The air measuring device of claim 8 further comprising:

a clamp to engage with an outside surface of the container to engage with the tube to hold the tube in place when the subject exhales air via the tube into the container.

10. An air volume measuring device to measure a residual lung volume in a body of a subject, the air volume measuring device comprising:
- a translucent expandable container with an open end and a closed end, the container having a length extending longer than its width;
- a semi-rigid strip coupled to the container to indicate when air pressure within the container is between a predetermined range;
- the container having a plurality of equally spaced radial demarcations extending from the closed end to the open end, a first of the demarcations to indicate a distance from a point below a bottom of a nose to the top of a head of the subject when the container is placed adjacent the subject, and a second of the demarcations to indicate a residual lung volume variable, when the semi-rigid strip indicates that air pressure within the container is between a predetermined pressure range, corresponding to a measured volume of air exhaled by the subject when the subject exhales air expanded within the body resulting from the subject moving from a deeper depth to a shallow depth in a pool of water after the subject empties air from its lungs into the pool at the deeper depth;
- a lung volume electronic computing device to determine residual lung volume based on a reading of the at least one of the radial demarcations indicating the residual lung volume variable in response to the strip indicating the air pressure within the container is between the predetermined range; and
- circuitry to determine the residual lung volume (V1) of the subject with the lung volume electronic computing device using the formula $V1=P2*MVOA/(P1-P2)$, where P1 is an underwater pressure determined based on the deeper depth and the water density, where P2 is an underwater pressure determined at the shallow depth based on the measurement of the shallow depth and the determined water density, and where MVOA is the measured volume of any potentially remaining air exhaled by the subject at the shallow depth after exhaling air by the subject at the deeper depth.

11. The air measuring device of claim 10, wherein the strip is substantially round with an outer lower lip integrally coupled at one end to the container and coupled at the lips other end to a wall that is coupled with an inner circular tab that raises when the air pressure within the container is between a predetermined range.

* * * * *